United States Patent
Beers

(10) Patent No.: US 7,179,808 B2
(45) Date of Patent: Feb. 20, 2007

(54) SUBSTITUTED HETEROARYL AND HETEROCYCLIC COMPOUNDS USEFUL IN TREATING INFLAMMATORY DISORDERS

(75) Inventor: Scott Beers, Flemington, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 375 days.

(21) Appl. No.: 10/612,187

(22) Filed: Jul. 2, 2003

(65) Prior Publication Data

US 2005/0014745 A1 Jan. 20, 2005

Related U.S. Application Data

(60) Provisional application No. 60/393,710, filed on Jul. 3, 2002.

(51) Int. Cl.
*A61K 31/535* (2006.01)
*A61K 31/425* (2006.01)
*A61K 31/405* (2006.01)
*C07D 417/10* (2006.01)
*C07D 277/20* (2006.01)
*C07D 209/04* (2006.01)
*C07D 295/00* (2006.01)

(52) U.S. Cl. .................. 514/236.8; 514/365; 514/415; 514/422; 544/133; 548/146; 548/469; 548/518

(58) Field of Classification Search .............. 548/146, 548/469, 518; 514/236.8, 365, 415, 422; 544/133
See application file for complete search history.

(56) References Cited

FOREIGN PATENT DOCUMENTS

| WO | WO 96/13264 | * | 5/1996 |
|---|---|---|---|
| WO | WO 96/13264 A | | 5/1996 |
| WO | WO 98/15274 A | | 4/1998 |
| WO | WO 99/18091 A | | 4/1999 |

OTHER PUBLICATIONS

Lau et al. "Evolution of a Series of Non-Qinoline Leukotriene D4 Receptor Antagonist; Synthesis and SAR of Benzothiazoles and Thiazoles Substituted Benzyl Alcohols as Potent LTD4 Antagonists" Biorganic & Medicinal Chemistry Letters, 1995, 1615-1620.*
McMurry, John "Organic Chemistry—Fourth Edition" Brooks/Cole Publishing Company, 1996, pp. 377-385, 603-604, 679-680, and 946-947.*
Malamas M.S. et al., "Azole phenoxy hydroxyureas as selective and orally active inhibitors to 5-lipoxygenase", Journal of Medicinal Chemistry, vol. 39, No. 1, Jan. 5, 1996.
PCT International Search Report, dated Dec. 19, 2003, for PCT Appln. No. PCT/US03/20781.

* cited by examiner

*Primary Examiner*—Kamal A. Saeed
*Assistant Examiner*—Joseph R. Kosack
(74) *Attorney, Agent, or Firm*—John Harbour

(57) ABSTRACT

This invention is directed to substituted heteroaryl and heterocyclic compounds as nicotinamide adenine dinucleotide oxidase hydride donor inhibitors useful in treating or ameliorating a reactive oxygen species mediated inflammatory disorder.

13 Claims, No Drawings

SUBSTITUTED HETEROARYL AND HETEROCYCLIC COMPOUNDS USEFUL IN TREATING INFLAMMATORY DISORDERS

CROSS-REFERENCE TO RELATED APPLICATIONS

This appllication claims the benefit of provisional application Ser. No. 60/393,710 filed on Jul. 3, 2002.

FIELD OF THE INVENTION

This invention relates to a series of substituted heteroaryl and heterocyclic compounds, pharmaceutical compositions and methods for use thereof in treating or ameliorating an inflammatory disorder. More particularly, the substituted heteroaryl and heterocyclic compounds of the present invention are nicotinamide adenine dinucleotide oxidase hydride donor inhibitors and are useful in treating or ameliorating a reactive oxygen species mediated inflammatory disorder.

BACKGROUND OF THE INVENTION

The nicotinamide adenine dinucleotides (NAD, NADH, NADP and NADPH) are essential cofactors in all living systems and function as hydride acceptors (NAD, NADP) and hydride donors (NADH, NADPH) in biochemical redox reactions. The six-step biosynthetic pathway begins with the oxidation of aspartate to iminosuccinic acid, which is then condensed with dihydroxyacetone phosphate to give quinolinic acid. Phosphoribosylation and decarboxylation of quinolinic acid gives nicotinic acid mononucleotide. Adenylation of this mononucleotide followed by amide formation completes the biosynthesis of NAD. An additional phosphorylation gives NADP (Begley, T P., et al., The Biosynthesis of Nicotinamide Adenine Dinucleotides in Bacteria, *Vitam. Horm.*, 2001, 61, 103–119).

The importance of reactive oxygen species (ROS) in the pathogenesis of inflammatory diseases is increasingly recognized. During inflammation, polymorphonuclear leucocytes (PMN) and macrophages become stimulated by lipopolysaccharide (LPS) and tumor necrosis factor alpha (TNF-α) as well as cytokines IFN-γ and interleukin-2 (IL-2). Stimulation results in the cellular assembly of a nicotinamide adenine dinucleotide oxidase hydride donor, in particular NADPH, a membrane bound enzyme which is the major source of ROS. The generation of ROS has been shown to be elevated up to 10 fold in patients with various inflammatory and autoimmune rheumatic diseases (R. Miesel, et al., Suppression of Inflammatory Arthritis by Simultaneous Inhibition of Nitric Oxide Synthase and NADPH Oxidase, *Free Radical Biology & Medicine*, 1996, 20(3), 75–81).

Two known inhibitors of NADPH Oxidase, diphenylene iodoniumchloride (DPI) and staurosporine have been shown to have antiinflammatory effects in mice with potassium peroxochromate arthritis. Daily doses of 2.8 μmol/kg of DPI and 30 nmol/kg staurosporine inhibited the arthritis by 50%. Complete inhibition was obtained with 10 mmol/kg DPI while 85% inhibition of the arthritis was achieved with 100 nmol staurosporine (R. Miesel, et al., Antiinflammatory Effects of NADPH Oxidase Inhibitors, *Inflammation*, 1995, 19(3), 347–362).

The antirheumatic drug Piroxicam has been shown to reduce levels of ROS in human patients with rheumatoid arthritis and osteoarthritis by 25% at pharmacological doses. In vitro studies showed that this inhibition was caused by interference of the activation of NADPH Oxidase (P. Biemond, et al., Superoxide Production by Polymorphonuclear Leucocytes in Rheumatoid Arthritis and Osteoarthritis: In vivo Inhibition by the Antirheumatic Drug Piroxicam Due to the Interference With the Activation of the NADPH Oxidase, *Annals of the Rheumatic Diseases*, 1986, 45, 249–255).

The deposition of β-amyloid in the brain is the key pathogenic event in Alzheimer's disease. Recently, β-amyloid has been shown to induce the stimulation of NADPH oxidase in human neutrophils and microglia in a dose dependent manner. The subsequent production of ROS is at least in part responsible for the neurodegenerative effects of β-amyloid (V. D. Bianca, et al., β-Amyloid Activates the $O_2$-Forming NADPH Oxidase in Microglia, Monocytes, and Neutrophils, *The Journal of Biological Chemistry*, 1999, 274, 15493–15499).

The object of the present invention is to provide substituted heteroaryl and heterocyclic compounds as nicotinamide adenine dinucleotide oxidase hydride donor inhibitors and a method for use of such compounds in treating or ameliorating a reactive oxygen species mediated inflammatory disorder.

SUMMARY OF THE INVENTION

The present invention relates to substituted heteroaryl and heterocyclic compounds of Formula (I):

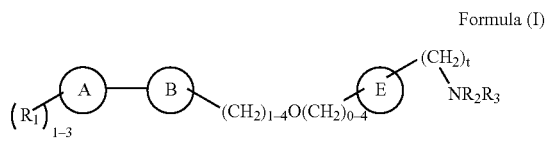

Formula (I)

wherein:

B is heteroarylene; wherein heteroarylene is selected from an aromatic monocyclic ring having five members of which at least one member is a N, O or S atom and which optionally contains one additional N atom;

A and E are independently phenylene or pyridinylene;

t is an integer from 1 to 4;

$R_1$ is selected from hydrogen, $C_{1-8}$alkyl, $C_{1-8}$alkoxy, $NH_2$, $NH(C_{1-8}$alkyl), $N(C_{1-8}$alkyl$)_2$, halogen or hydroxy; wherein $R_1$ is substituted on the 3, 4 or 5 position of the "A" ring;

$R_2$ and $R_3$ are independently selected from hydrogen, $C_{1-8}$alkyl-$R_4$ or $C_{3-6}$cycloalkyl;

$R_4$ is selected from $(C_{1-8})$alkoxy, $NH_2$, $NH(C_{1-8}$alkyl), $N(C_{1-8}$alkyl$)_2$, (halo$)_{1-3}$, hydroxy, $C_{3-6}$cycloalkyl-$R_5$, heterocyclyl-$R_5$, aryl-$R_5$ or heteroaryl-$R_5$; and, $R_5$ is 1 to 2 substituents selected from hydrogen, $C_{1-8}$alkyl or $(C_{1-8})$alkoxy (wherein alkoxy is substituted on a carbon atom);

and pharmaceutically acceptable salts thereof.

The present invention also provides a method for treating or ameliorating a reactive oxygen species mediated inflammatory disorder in a subject in need thereof comprising administering to the subject a therapeutically effective amount of a compound selected from Formula (I).

In a preferred embodiment of the method of the present invention, the reactive oxygen species is selected from the group consisting of superoxide, hydrogen peroxide, hydroxyl radical and HOCl.

DETAILED DESCRIPTION OF THE INVENTION

Aspects of the present invention include compounds of Formula (I) wherein B is selected from oxazolylene, thiazolylene, imidazolylene, pyrimidinylene, pyrazinylene or triazinylene.

Another aspect of the present invention includes compounds of Formula (I) wherein B is selected from oxazolylene, thiazolylene or imidazolylene.

Aspects of the present invention include compounds of Formula (I) wherein t is an integer from 1 to 2.

Another aspect of the present invention includes compounds of Formula (I) wherein t is an integer 1.

Aspects of the present invention include compounds of Formula (I) wherein $R_1$ is selected from hydrogen, $C_{1-4}$alkyl, $C_{1-4}$alkoxy, $NH_2$, $NH(C_{1-4}alkyl)$, $N(C_{1-4}alkyl)_2$, halogen or hydroxy; wherein $R_1$ is substituted on the 3, 4 or 5 position of the "A" ring.

Another aspect of the present invention includes compounds of Formula (I) wherein $R_1$ is selected from hydrogen, $C_{1-4}$alkyl, $C_{1-4}$alkoxy or halogen; wherein $R_1$ is substituted on the 4 position of the "A" ring.

Aspects of the present invention include compounds of Formula (I) wherein $R_2$ and $R_3$ are independently selected from hydrogen, $C_{1-4}$alkyl-$R_4$ or $C_{3-6}$cycloalkyl.

Aspects of the present invention include compounds of Formula (I) wherein $R_4$ is selected from $C_{1-4}$alkoxy, $NH_2$, $NH(C_{1-4}alkyl)$, $N(C_{1-4}alkyl)_2$, $(halo)_{1-3}$, hydroxy, $C_{3-6}$cycloalkyl-$R_5$, heterocyclyl-$R_5$, aryl-$R_5$ or heteroaryl-$R_5$.

Another aspect of the present invention includes compounds of Formula (I) wherein $R_4$ is selected from heterocyclyl-$R_5$ or heteroaryl-$R_5$.

Another aspect of the present invention includes compounds of Formula (I) wherein $R_4$ is selected from pyrrolidinyl-$R_5$, morpholinyl-$R_5$, furyl-$R_5$ or indolyl-$R_5$.

Aspects of the present invention include compounds of Formula (I) wherein $R_5$ is 1 to 2 substituents selected from hydrogen, $C_{1-4}$alkyl or $(C_{1-4})$alkoxy (wherein alkoxy is substituted on a carbon atom).

Exemplifying the invention is a compound of Formula (I) selected from a compound of Formula (Ia)

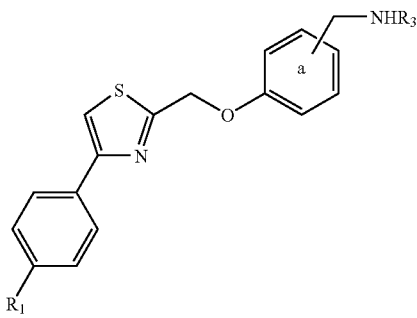

Formula (Ia)

wherein $R_1$, the position "a" and $R_3$ are dependently selected from:

| Cpd | $R_1$ | a | | $R_3$ |
|-----|-------|---|---|-------|
| 1 | Cl, | 3 | and | n-propyl; |
| 1a | Cl, | 4 | and | n-propyl; |

-continued

| Cpd | $R_1$ | a | | $R_3$ |
|-----|-------|---|---|-------|
| 2 | Cl, | 3 | and | isobutyl; |
| 3 | Cl, | 3 | and | cyclopentyl; |
| 4 | Cl, | 3 | and | cyclohexyl; |
| 5 | Cl, | 3 | and | cyclopropyl; |
| 6 | Cl, | 3 | and | $CH_2$-(1-Me)-2-pyrrolidinyl; |
| 7 | Cl, | 3 | and | $(CH_2)_2$-4-morpholinyl; |
| 8 | Cl, | 3 | and | (5-Me)furfuryl; |
| 9 | Cl, | 3 | and | $(CH_2)_2$-(5-OMe)-1H-indol-3-yl; |
| 10 | Cl, or | 4 | and | cyclopentyl; |
| 11 | Cl, | 3 | and | H. |

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201–217; *J. Pharm. Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "independently" means that when a group is substituted with more than one substituent that the substituents may be the same or different. The term "dependently" means that the substituents are specified in an indicated combination of structure variables.

Unless specified otherwise, the term "alkyl" refers to a saturated straight or branched chain typically consisting solely of 1–8 hydrogen substituted carbon atoms, 1–6 hydrogen substituted carbon atoms or 1–4 hydrogen substituted carbon atoms. The term "($C_{a-b}$)" (where a and b are integers) refers to an alkyl chain containing from a to b carbon atoms inclusive. Accordingly, ($C_{1-4}$)alkyl denotes an alkyl chain containing 1, 2, 3 or 4 carbon atoms. Alkyl chains are optionally substituted within the alkyl chain or on a terminal carbon atom. The term "($C_{a-b}$) alkylene" refers to an alkyl group functioning as a linking group.

The term "($C_{a-b}$)alkoxy" refers to —O—($C_{a-b}$)alkyl, where alkyl is as previously defined.

The term "($C_{a-b}$)cycloalkyl" refers to a saturated or partially unsaturated monocyclic alkyl ring consisting of 3–8 hydrogen substituted carbon atoms or a saturated or partially unsaturated bicyclic ring consisting of 9 or 10 hydrogen substituted carbon atoms. Examples include, and are not limited to, cyclopropyl, cyclobutyl, cyclopentyl, cyclohexyl or cycloheptyl. The term "cycloalkylene" refers to a cycloalkyl group functioning as a linking group.

The term "heterocyclyl" refers to a saturated or partially unsaturated ring having five members of which at least one member is a N, O or S atom and which optionally contains one additional O atom or one additional N atom, wherein at most two nitrogen atoms are adjacent; a saturated or partially unsaturated ring having six members of which one, two or three members are a N atom, wherein at most two nitrogen atoms are adjacent; or, a saturated or partially unsaturated bicyclic ring having nine or ten members of which at least one member is a N, O or S atom and which optionally contains one, two or three additional N atoms, wherein at most two nitrogen atoms are adjacent. Examples include, and are not limited to, pyrrolinyl, pyrrolidinyl, imidazolinyl, imidazolidinyl, pyrazolinyl, pyrazolidinyl, piperidinyl, morpholinyl or piperazinyl. The term "heterocyclylene" refers to a heterocyclyl group functioning as a linking group.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl or anthracenyl. The term "arylene" refers to an aryl group functioning as a linking group.

The term "heteroaryl" refers to an aromatic monocyclic ring system containing five members of which at least one member is a N, O or S atom and which optionally contains one, two or three additional N atoms, wherein at most two nitrogen atoms are adjacent; an aromatic monocyclic ring having six members of which one, two or three members are a N atom, wherein at most two nitrogen atoms are adjacent; an aromatic bicyclic ring having nine members of which at least one member is a N, O or S atom and which optionally contains one, two or three additional N atoms, wherein at most two nitrogen atoms are adjacent; an aromatic bicyclic ring having ten members of which one, two or three members are a N atom, wherein at most two nitrogen atoms are adjacent; or, an aromatic tricyclic ring system containing 13 or 14 members of which at least one member is a N, O or S atom and which optionally contains one, two or three additional N atoms, wherein at most two nitrogen atoms are adjacent. Examples include, and are not limited to, furyl, thienyl, pyrrolyl, oxazolyl, thiazolyl, imidazolyl, pyrazolyl, isoxazolyl, isothiazolyl, thiadiazolyl, pyrimidinyl, pyrazinyl and triazinyl. The term "heteroarylene" refers to a heteroaryl group functioning as a linking group.

An embodiment of the present invention includes the use of a compound of Formula (I) for the preparation of a pharmaceutical composition or medicament thereof for treating or ameliorating a reactive oxygen species mediated inflammatory disorder in a subject in need thereof.

An embodiment of the present invention includes a method for treating or ameliorating a reactive oxygen species mediated inflammatory disorder in a subject in need thereof comprising administering to the subject a therapeutically effective amount of an instant compound or pharmaceutical composition thereof.

In a method for treating or ameliorating a reactive oxygen species mediated inflammatory disorder, the term "reactive oxygen species" includes, and is not limited to, a reactive oxygen species selected from a superoxide, hydrogen peroxide, hydroxyl radical or HOCl reactive oxygen species.

A reactive oxygen species mediated inflammatory disorder includes, and is not limited to, phosphorylation mediated disorders, polymorphonuclear leucocyte mediated disorders, macrophage mediated disorders, lipopolysaccharide mediated disorders, tumor necrosis factor-α mediated disorders, cytokine IFN-γ mediated disorders, interleukin-2 mediated disorders, inflammatory arthritis, potassium peroxochromate arthritis, rheumatoid arthritis, osteoarthritis or Alzheimer's disease.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation and the advancement of the disease condition. In addition, factors associated with the particular subject being treated, including subject age, weight, diet and time of administration, will result in the need to adjust the dose to an appropriate therapeutic level.

A therapeutically effective amount for use of the instant compounds or a pharmaceutical composition thereof comprises a dose range of from about 0.001 mg to about 1,000 mg, a dose range of from about 0.1 mg to about 500 mg or a dose range of from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

The terms used in describing the invention are commonly used and known to those skilled in the art. As used herein, the following abbreviations have the indicated meanings:

| | |
|---|---|
| DEAD | diethylazodicarboxylate |
| DIBAL | diisobutylaluminum hydride |
| TPP | triphenylphosphine |
| mp | melting point |

| -continued | | |
|---|---|---|
| HBSS | | |
| h | Hour | |
| min | Minute | |
| rt | Room temperature | |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

A bromoacetyl and $R_1$ substituted "A" ring Compound A1 can be reacted with an amino and an X heteroatom (wherein X is selected from S, O, $NH_2$, $NH(C_{1-8}alkyl)$ or $N(C_{1-8}alkyl)_2$) substituted Compound A2 in an alcohol such as ethanol to yield an intermediate Compound A3. The amino and X heteroatom substituted on Compound A2 react with the bromoacetyl substituent of Compound A1 to form the "B" ring of Compound A3; the length of the alkyl chains may be varied as indicated.

Reduction of the Compound A3 ester with diisobutyl aluminum hydride gives a hydrolyzed Compound A4. A Mitsunobu reaction of Compound A4 with a hydroxy substituted Compound A5 (when $(CH_2)_0$) affords an intermediate Compound A6 using coupling reagents such as TPP and DEAD. When Compound A5 is $(CH_2)_{1-4}$, then the Compound A4 hydroxy must be converted to a leaving group by either mesylation or halogenation using reagents known to those skilled in the art and the Compound A5 hydroxy must be converted to an alkoxide base by reaction with a suitable base such as NaH. Reductive amination of the aldehyde Compound A6 with a $NHR_2R_3$ Compound A7 gives the target Compound A8.

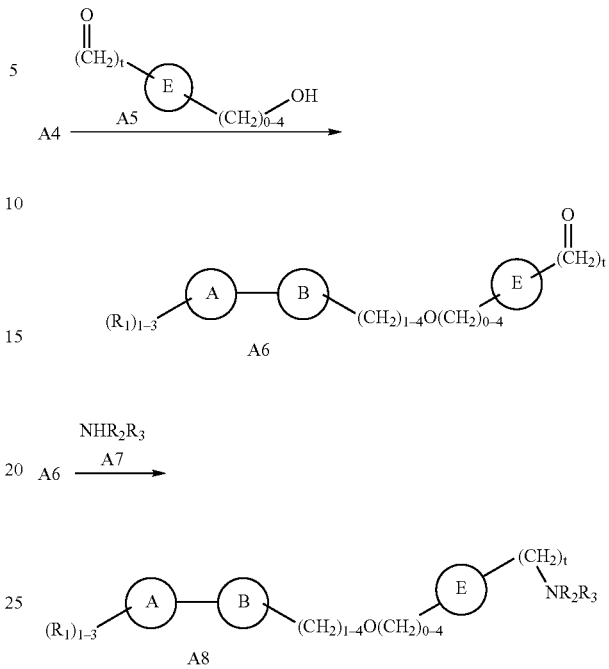

Scheme B

An $R_1$ substituted bromoacetophenone Compound B1 can be reacted with an X substituted ethyl oxamate Compound B2 in an alcohol such as ethanol to yield an intermediate Compound B3. Reduction of the ester of Compound B3 with diisobutyl aluminum hydride gives an alcohol Compound B4. Mitsunobu reaction of Compound B4 with either a 3-hydroxy or 4-hydroxy substituted benzaldehyde Compound B5 affords a corresponding intermediate Compound B6. Reductive amination of the aldehyde Compound B6 with a substituted amine Compound B7 gives the target Compound B8, wherein the "B" ring comprises 5 members.

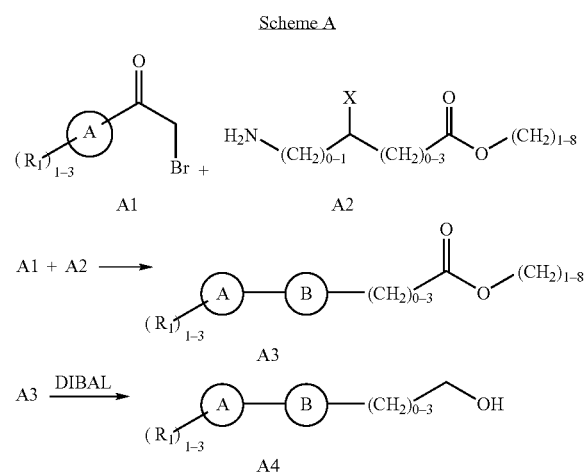

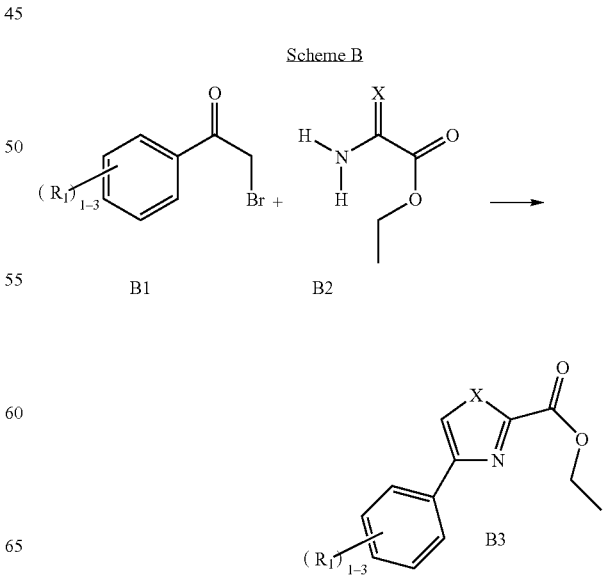

-continued

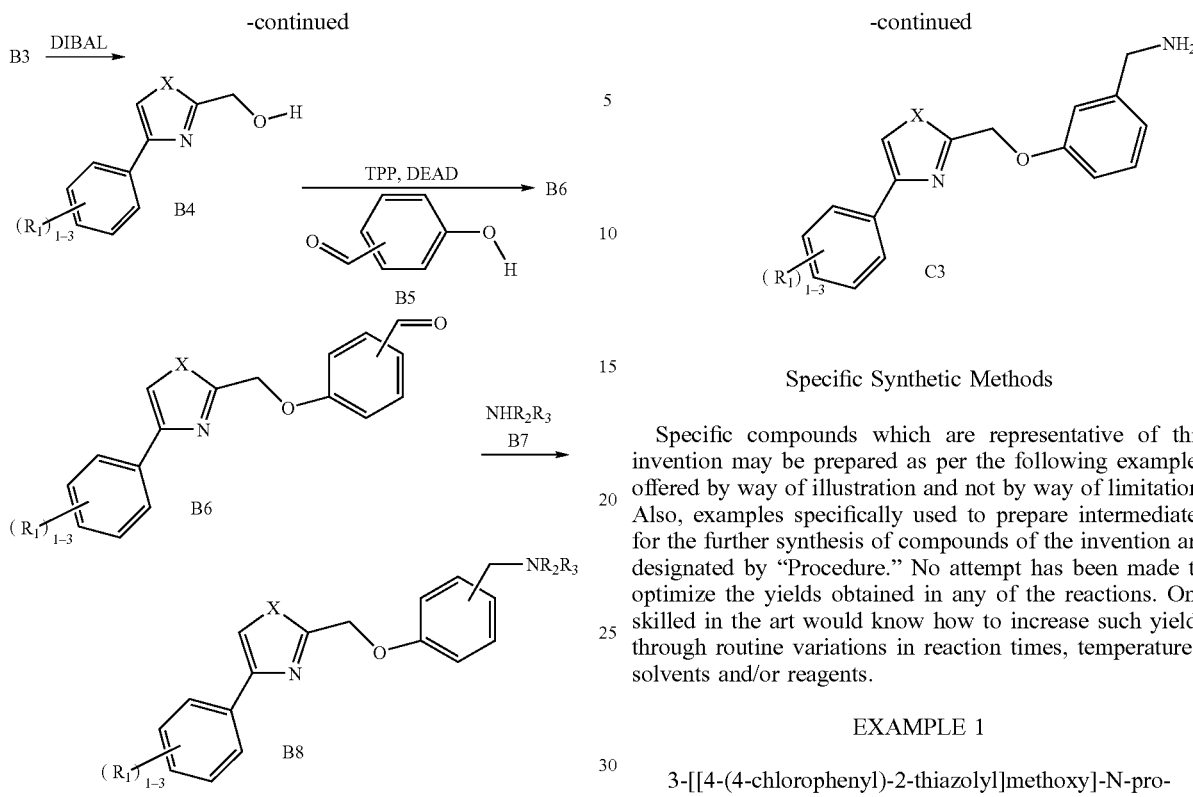

Scheme C

The aldehyde Compound B6 from Scheme B is reduced with sodium borohydride to give an alcohol Compound C1. A Mitsunobu reaction of Compound C1 with phthalimide affords an intermediate Compound C2. Deprotection of Compound C2 with hydrazine yields the target Compound C3, wherein NR$_2$R$_3$ is on the 3 position of the phenyl ring.

Scheme C

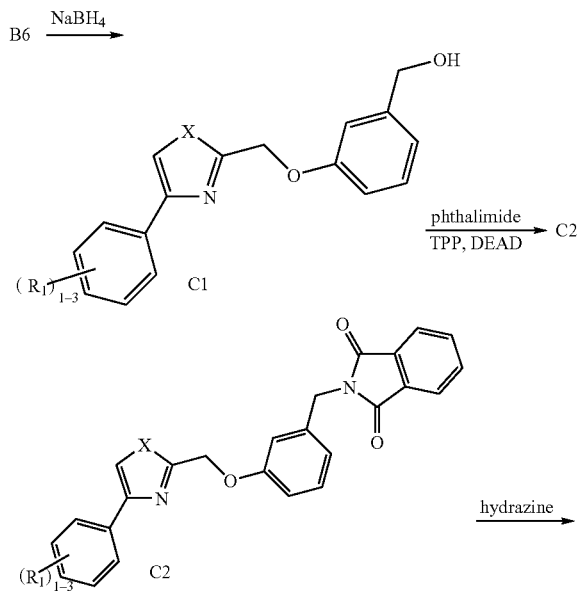

Specific Synthetic Methods

Specific compounds which are representative of this invention may be prepared as per the following examples offered by way of illustration and not by way of limitation. Also, examples specifically used to prepare intermediates for the further synthesis of compounds of the invention are designated by "Procedure." No attempt has been made to optimize the yields obtained in any of the reactions. One skilled in the art would know how to increase such yields through routine variations in reaction times, temperatures, solvents and/or reagents.

EXAMPLE 1

3-[[4-(4-chlorophenyl)-2-thiazolyl]methoxy]-N-propyl-benzenemethanamine (Cpd 1)

Following the protocol of Scheme B, a 2-Bromo-4'-chloroacetophenone (3.69 grams) (See Scheme B, Compound B1, wherein R$_2$ is chloro) was dissolved in ethanol (100 mL). Thiooxamate (2.10 grams) (Scheme B, Compound B2) and pyridine (1.30 mL) were added to the mixture which was stirred at reflux for 1 hour and then poured into ice-water. The solid was filtered to give an ethyl-2-[4-(4-chlorophenyl)]thiazolylcarboxylate (Scheme B, Compound B3). Mp=102–103° C.; MS 268 (MH$^+$); $^1$HNMR (CDC$_3$) δ 7.87 (d, 2H), 7.75 (s, 1H), 7.43 (d, 2H), 4.52 (q, 2H), 1.47 (t, 3H).

The carboxylate (6.61 grams) (Scheme B, Compound B3) was dissolved in dichloromethane (200 mL) and cooled to −78° C. A solution of diisobutylaluminum hydride (33 mL, 1.5 M sol'n) was added. The reaction was stirred for 1.5 hours and then warmed to ambient temperature. 1 N aqueous sodium hydroxide (200 mL) was added and the layers were separated. The organic layer was dried over sodium sulfate, concentrated and eluted through a silica gel plug using ethyl acetate as the eluent to give a 2-[4-(4-chlorophenyl)thiazolyl]carbinol (Scheme B, Compound B4). Mp 152.5–153.5° C.; MS 226 (MH$^+$); $^1$HNMR (DMSO) δ 6.15 (t, 1H, OH), 4.80 (d, 2H).

The carbinol (1.41 grams) (Scheme B, Compound B4) was dissolved in tetrahydrofuran (70 mL). 3-hydroxybenzaldehyde (Scheme B, Compound B5) (0.76 grams), triphenylphosphine (1.83 grams) and diethylazodicarboxylate (1.10 mL) were added to the mixture which was stirred under nitrogen for 18 hours. Ethyl acetate (50 mL) was then added and the solution was washed with an aqueous 1 N sodium hydroxide solution, followed by water. The organic layer was concentrated and chromatographed on a silica gel column eluted with hexane-ethyl acetate 3:1 to give a 2-(3-formyl)phenoxymethyl-4-(4-chlorophenyl)thiazole (Scheme B, Compound B6). Mp 129.5–130° C. $^1$HNMR (CDCl$_3$) δ 10.00 (s, 1H), 5.48 (s, 2H).

The thiazole (0.31 grams) (Scheme B, Compound B6) was dissolved in dichloromethane (20 mL). Propylamine (0.08 mL) (Scheme B, Compound B7; wherein R$_1$ is two substituents independently selected from hydrogen and n-propyl), sodiumtriacetoxy borohydride (0.32 grams) and acetic acid (2 drops) were added to the mixture which was then stirred for 18 hours. Aqueous sodium hydroxide (20 mL of 1 N sol'n) was then added and the layers were separated. The organic layer was concentrated and column chromatographed (silica gel) using a mobile phase of dichloromethane-methanol 19:1 to give Compound 1. Mp 63.5–64.5° C.; MS 373 (MH$^+$).

Using the procedure of Example 1 and the appropriate reagents and starting materials known to those skilled in the art, other compounds of the present invention may be prepared including, but not limited to:

| Cpd | Name | mp (° C.) | MS (MH$^+$) |
|---|---|---|---|
| 1a | 4-[[4-(4-chlorophenyl)-2-thiazolyl]methoxy]-N-propyl-benzenemethanamine | 63.5–64.5 | 373 |
| 2 | 3-[[4-(4-chlorophenyl)-2-thiazolyl]methoxy]-N-(3-methylpropyl)-benzenemethanamine | 86–88 | 387 |
| 3 | 3-[[4-(4-chlorophenyl)-2-thiazolyl]methoxy]-N-cyclopentyl-benzenemethanamine | 94–94.5 | 399 |
| 4 | 3-[[4-(4-chlorophenyl)-2-thiazolyl]methoxy]-N-cyclohexyl-benzenemethanamine | 85–86 | 413 |
| 5 | 3-[[4-(4-chlorophenyl)-2-thiazolyl]methoxy]-N-cyclopropyl-benzenemethanamine | 80.5–81.5 | 371 |
| 6 | N-[[3-[[4-(4-chlorophenyl)-2-thiazolyl]methoxy]phenyl]methyl]-1-methyl-2-pyrrolidinemethanamine.(HCl)$_2$ | — | 442 |
| 7 | 4-[2-[3-[[4-(4-chlorophenyl)-2-thiazolyl]methoxy]phenyl]ethyl]-morpholine.(HCl)$_2$ | — | 444 |
| 8 | 4-(4-chlorophenyl)-2-[[3-[(5-methyl-2-furanyl)methyl]phenoxy]methyl]-thiazole | 83–84.5 | 425 |
| 9 | N-[[3-[[4-(4-chlorophenyl)-2-thiazolyl]methoxy]phenyl]methyl]-5-methoxy-1H-indole-3-ethanamine.HCl | — | 504 |
| 10 | 4-[[4-(4-chlorophenyl)-2-thiazolyl]methoxy]-N-cyclopentyl-benzenemethanamine | 125.5–126.5 | 399 |

EXAMPLE 2

3-[[4-(4-chlorophenyl)-2-thiazolyl]methoxy]-benzenemethanamine (Compound 11)

Following the protocol of Scheme C, the thiazole compound prepared in Example 1 (2.20 grams) (Scheme B, Compound B6, wherein R$_2$ is chloro) was dissolved in ethanol (100 mL). Sodium borohydride (0.25 grams) was added to the mixture which was then stirred at ambient temperature for 4 hours before being quenched with aqueous ammonium chloride. The product was extracted with dichloromethane to give a 3-[[4-(4-chlorophenyl)-2-thiazolyl] methoxy]phenylmethyl alcohol (See Scheme C, Compound C1). Mp 141–142.5° C.; MS 332 (MH$^+$);

$^1$HNMR (DMSO) δ 8.24 (s, 1H), 5.50 (s, 2H), 4.48 (d, 2H).

The phenylmethylalcohol compound (1.98 grams) (Scheme C, Compound C1) was dissolved in tetrahydrofuran (100 mL). Triphenylphosphine (1.84 grams), phthalimide (1.03 grams) and diethylazodicarboxylate (1.10 mL) were added to the mixture which was then stirred for 16 hours before being evaporated in vacuo. The residue was column chromatographed (silica gel) using a mobile phase of hexane-ethyl acetate 2:1 to give a N-[3-[[4-(4-chlorophenyl)-2-thiazolyl]methoxy]phenylmethyl]phthalimide (Scheme C, Compound C2). Mp 156.5–157.5° C.; MS 461 (MH$^+$).

The phthalimide compound (1.65 grams) (Scheme C, Compound C2) was suspended in ethanol (100 mL). Hydrazine hydrate (1 mL) was added and the reaction was stirred at reflux for 2 hours before being cooled to ambient temperature. The mix was then filtered and the filtrate was evaporated. The crude solid was dissolved in dichloromethane, then sequentially washed with 1 N potassium hydroxide and water. The organic layer was then evaporated to give 3-[[4-(4-chlorophenyl)-2-thiazolyl]methoxy]benzenemethanamine Compound 11. Mp 117–118.5° C.; MS 331 (MH$^+$); $^1$HNMR (CDCl$_3$) δ 7.85 (d, 2H), 7.50 (s, 1H), 7.40 (d, 2H), 5.43 (s, 2H), 3.86 (s, 2H).

BIOLOGICAL EXAMPLES

The compounds of the present invention are useful as inhibitors of a nicotinamide adenine dinucleotide oxidase hydride donor. The following biological examples demonstrate the use of the instant compounds in a method for treating or ameliorating a reactive oxygen species mediated disease.

Example 1

Oxidase Inhibition Assay

Whole cells (human neutrophils) are incubated with a pro-inflammatory agonist phorbol myristate acetate (PMA) in the presence or absence of test compound to measure the superoxide-mediated reduction of Cytochrome c at 550 nm. Inhibition of the oxidase is determined by a decreased absorbance at 550 nm, in response to test compound, relative to the absorbance seen with a vehicle control.

Method

The buffy coat from one unit of blood is split evenly into four 50 mL tubes. To each tube 30 mL 3% Dextran (in 0.9% NaCl) is added and the tubes are inverted to mix. Tubes are allowed to sit undisturbed for 25 minutes. The resulting supernatant is recovered into four fresh tubes and centrifuged for 10 minutes at 600×g, 4° C. The supernatant is discarded and pellets are resuspended in 35 mL 0.9% saline. 10 mL Ficoll-Paque PLUS (Pharmacia Biotech AB) is layered beneath the cell suspension and centrifuged at 600×g for 40 minutes at room temperature. The supernatant is again discarded and tubes are tapped to loosen the resulting pellets. 20 mL 0.2% ice cold saline is added for 30 seconds followed by 20 mL 1.6% ice cold saline to lyse the remaining erythrocytes in the pellets. The pellets are centrifuged for 10 minutes at 600×g, 4° C., and the supernatant is discarded. The neutrophil pellets are resuspended in HBSS-glucose buffer (1 mg/mL), adding 2.5 mL to each tube for a total volume of 10 mL. The cell suspension is then counted on a hemocytometer.

The cell suspension is diluted to a concentration of $5\times10^6$/mL in HBSS-glucose and treated with 1 µg/mL Cytochalasin B (5 mg/mL DMSO) for 10 minutes at 37° C.

in a shaking water bath. Cells are diluted to $6 \times 10^5$ cells/mL in 92 μM Cytochrome c for a final concentration of $5 \times 10^4$ cells/well.

The NADPH-oxidase assay is run on a Biomek 2000 workstation. The workstation adds 2.5 μl compound per well from source plates plus 12.5 μL per well 4 μM PMA (agonist). This volume is brought up to 100 μL total per well in the assay plates upon the addition of the prepared cells (85 μL). The final concentration of drug is 25 μM and PMA is 0.5 μM under these conditions.

The QC curve is a dose-responsive curve (from about 31.25 nM to about 4000 nM) for competitive binding against a known oxidase inhibitor such as DPI (diphenylene iodonium chloride). The following format was used for each compound tested:

| Wells | % Inhibition | Inhibitor | Agent added |
|---|---|---|---|
| A–D | Control wells | 2.5 μL vehicle | 12.5 μL (agonist) |
| E–F | Blank wells | 2.5 μL vehicle | 12.5 μL (HBSS) |
| G–H | ~70% (at 250 nm) | 2.5 μL of 10 μM DPI | 12.5 μL (agonist) |

The plates are incubated for 1 hour at 37° C. without $CO_2$. The plates are then incubated at room temperature for 30 minutes and the absorbance is read at 550 nm. The data for instant compounds of the invention is shown in Table 1.

TABLE 1

| Cpd | $IC_{50}$ (μM) |
|---|---|
| 1 | 1.65 |
| 2 | 2.5 |
| 3 | 0.04 |
| 4 | 0.13 |
| 5 | 3.45 |
| 6 | 10 |
| 7 | 1.47 |
| 8 | 0.7 |
| 9 | 0.3 |
| 10 | 0.7 |
| 11 | 1.9 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

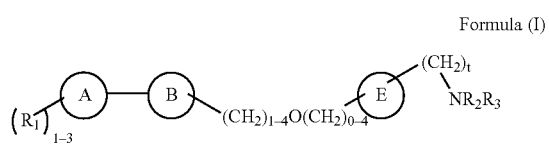

Formula (I)

wherein:
B is thiazole;
A and E are phenylene;
t is an integer from 1 to 4;

$R_1$ is selected from hydrogen, $C_{1-8}$alkyl, $C_{1-8}$alkoxy, $NH_2$, $NH(C_{1-8}alkyl)$, $N(C_{1-8}alkyl)_2$, halogen or hydroxy; wherein $R_1$ is substituted on the 3, 4 or 5 position of the "A" ring;

$R_2$ and $R_3$ are independently selected from hydrogen, $C_{1-8}$alkyl-$R_4$ or $C_{3-6}$cycloalkyl;

$R_4$ is selected from $(C_{1-8})$alkoxy, $NH_2$, $NH(C_{1-8}alkyl)$, $N(C_{1-8}alkyl)_2$, $(halo)_{1-3}$, hydroxy, $C_{3-6}$cycloalkyl-$R_5$, heterocyclyl-$R_5$, aryl-$R_5$ or heteroaryl-$R_5$; and, $R_5$ is 1 to 2 substituents selected from hydrogen, $C_{1-8}$alkyl or $(C_{1-8})$alkoxy (wherein alkoxy is substituted on a carbon atom);

and pharmaceutically acceptable salts thereof.

2. The compound of claim 1 wherein t is an integer from 1 to 2.

3. The compound of claim 1 wherein t is an integer 1.

4. The compound of claim 1 wherein $R_1$ is selected from hydrogen, $C_{1-4}$alkyl, $C_{1-4}$alkoxy, $NH_2$, $NH(C_{1-4}alkyl)$, $N(C_{1-4}alkyl)_2$, halogen or hydroxy; wherein $R_1$ is substituted on the 3, 4 or 5 position of the "A" ring.

5. The compound of claim 1 wherein $R_1$ is selected from hydrogen, $C_{1-4}$alkyl, $C_{1-4}$alkoxy or halogen; wherein $R_1$ is substituted on the 4 position of the "A" ring.

6. The compound of claim 1 wherein $R_2$ and $R_3$ are independently selected from hydrogen, $C_{1-4}$alkyl-$R_4$ or $C_{3-6}$cycloalkyl.

7. The compound of claim 1 wherein $R_4$ is selected from $C_{1-4}$alkoxy, $NH_2$, $NH(C_{1-4}alkyl)$, $N(C_{1-4}alkyl)_2$, $(halo)_{1-3}$, hydroxy, $C_{3-6}$cycloalkyl-$R_5$, heterocyclyl-$R_5$, aryl-$R_5$ or heteroaryl-$R_5$.

8. The compound of claim 1 wherein $R_4$ is selected from heterocyclyl-$R_5$ or heteroaryl-$R_5$.

9. The compound of claim 1 wherein $R_4$ is selected from pyrrolidinyl-$R_5$, morpholinyl-$R_5$, furyl-$R_5$ or indolyl-$R_5$.

10. The compound of claim 1 wherein $R_5$ is 1 to 2 substituents selected from hydrogen, $C_{1-4}$alkyl or $(C_{1-4})$alkoxy (wherein alkoxy is substituted on a carbon atom).

11. The compound of claim 1 wherein the compound of Formula (I) is selected from a compound of Formula (Ia):

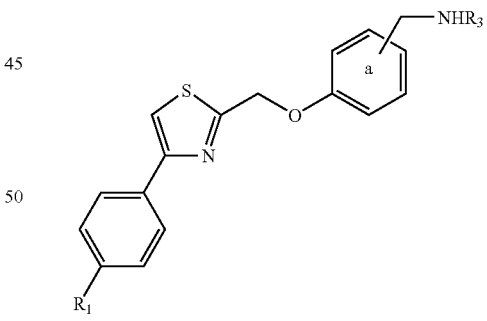

Formula (Ia)

wherein $R_1$, position "a" and $R_3$ are dependently selected from:

| $R_1$ | a | | $R_3$ |
|---|---|---|---|
| Cl, | 3 | and | n-propyl; |
| Cl, | 4 | and | n-propyl; |
| Cl, | 3 | and | isobutyl; |
| Cl, | 3 | and | cyclopentyl; |
| Cl, | 3 | and | cyclohexyl; |

-continued

| $R_1$ | a | | $R_3$ |
|---|---|---|---|
| Cl, | 3 | and | cyclopropyl; |
| Cl, | 3 | and | $CH_2$-(1-Me)-2-pyrrolidinyl; |
| Cl, | 3 | and | $(CH_2)_2$-4-morpholinyl; |
| Cl, | 3 | and | (5-Me)furfuryl; |
| Cl, | 3 | and | $(CH_2)_2$-(5-OMe)-1H-indol-3-yl; |
| Cl, or | 4 | and | cyclopentyl; |
| Cl, | 3 | and | H. |

12. A method for treating or ameliorating a reactive oxygen species mediated inflammatory disorder wherein the disorder is selected from inflammatory arthritis, potassium peroxochromate arthritis, rheummatoid arthritis, or osteoarthritis in a subject in need thereof comprising administering to the subject a therapeutically effective amount of the compound of claim 1.

13. The method of claim 12 wherein the therapeutically effective amount of the compound of claim 1 is from about 0.001 mg/kg/day to about 1000 mg/kg/day.

* * * * *